United States Patent [19]

Sasaki

[11] Patent Number: 4,764,164
[45] Date of Patent: Aug. 16, 1988

[54] IONTOPHORESIS DEVICE

[75] Inventor: Minoru Sasaki, Yokohama, Japan

[73] Assignee: Kabushiki Kaisya Advance Kaihatsu Kenkyujo, Tokyo, Japan

[21] Appl. No.: 792,245

[22] Filed: Oct. 30, 1985

Related U.S. Application Data

[63] Continuation of Ser. No. 646,116, Aug. 31, 1984, abandoned.

[30] Foreign Application Priority Data

Sep. 1, 1983 [JP] Japan .............................. 58-159076
Mar. 6, 1984 [JP] Japan .............................. 59-41440
Jul. 23, 1984 [JP] Japan .............................. 59-151310

[51] Int. Cl.$^4$ ............................................. A61M 1/30
[52] U.S. Cl. .................................................... 604/20
[58] Field of Search ................... 128/419 D, 422, 783, 128/741, 734; 604/20

[56] References Cited

U.S. PATENT DOCUMENTS

| | | | |
|---|---|---|---|
| 2,695,021 | 11/1954 | Touzel | 604/20 |
| 3,805,795 | 4/1974 | Denniston et al. | 128/419 D |
| 3,902,502 | 9/1975 | Liss et al. | 128/422 |
| 4,019,510 | 4/1977 | Ellis | 604/20 |
| 4,109,645 | 8/1978 | Bacchelli | 128/734 |
| 4,141,359 | 2/1979 | Jacobsen et al. | |
| 4,149,533 | 4/1979 | Ishikawa et al. | 604/20 |
| 4,301,794 | 11/1981 | Tapper | |
| 4,340,047 | 7/1982 | Tapper et al. | 604/20 |
| 4,416,289 | 11/1983 | Bresler | 128/207.14 |
| 4,474,570 | 10/1984 | Ariura et al. | |

FOREIGN PATENT DOCUMENTS

| | | | |
|---|---|---|---|
| 138347 | 4/1985 | European Pat. Off. | 604/20 |
| 860957 | 1/1941 | France | 604/20 |
| 2500689 | 8/1982 | France | 604/20 |
| 2104388 | 3/1983 | United Kingdom | 604/20 |
| 651805 | 3/1979 | U.S.S.R. | 604/20 |
| 1074542 | 2/1984 | U.S.S.R. | 604/20 |
| 1146061 | 3/1985 | U.S.S.R. | 604/20 |

Primary Examiner—Lee S. Cohen
Assistant Examiner—David Shay
Attorney, Agent, or Firm—Finnegan, Henderson, Farabow, Garrett & Dunner

[57] ABSTRACT

A device for iontophoresis including an electric source, a pulse generator, a working electrode, and a counter electrode is described. This device has a circuit for discharging the charges accumulated in said electrodes during each intermission period of therapeutic pulses generated by said pulse generator (i.e., a circuit for effecting the depolarization between the above-mentioned both electrodes during each intermission period of therapeutic pulses).

This device can be directly and very easily applied to the human skin, without causing undesirable irritation in the skin, especially without causing burns and rubefaction in the skin.

8 Claims, 10 Drawing Sheets

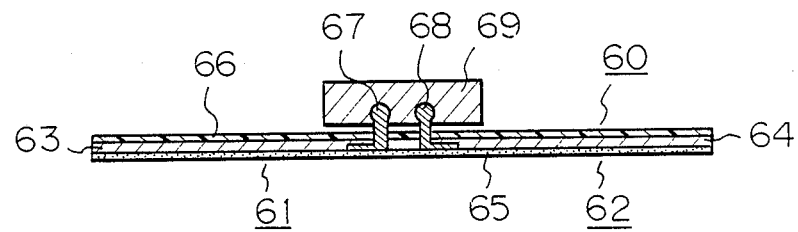
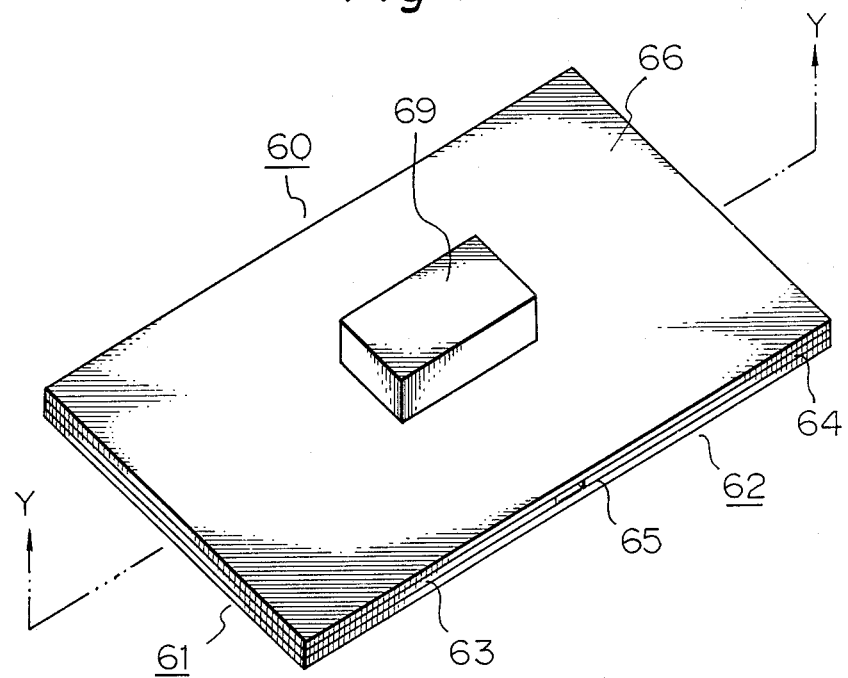

IONTOPHORESIS DEVICE

This application is a continuation of application Ser. No. 646,116, filed Aug. 31, 1984, now abandoned.

BACKGROUND OF THE INVENTION

1. Field of the Invention

The present invention relates to an iontophoresis device for epidermal application. More specifically, it relates to an iontophoresis device having a light weight and capable of direct and very easy application to the human skin, without causing undesirable irritation in the skin.

2. Description of the Prior Art

Recently, iontophoresis has gained increased attention as an effective method for topical application of ionic agents or drugs by promoting absorption through the skin. Iontophoresis techniques are disclosed in, for example, Glass J. M. et al., Int. J. Dermatol. 19,519 (1980); Russo J., Am. J. Hosp. Pharm. 37,843 (1980); Gangarosa L. P. et al., J. Pharmacol. Exp. Ther. 212,377 (1980); Kwon B. S. et al., J. Infect. Dis 140,1014 (1979); Hill J. M. et al., Ann. NY. Acad. Sci. 284,604 (1977), and Tannebaum M. Phys. Ther. 60,792 (1980).

The iontophoresis disclosed in these prior arts is usually carried out by connecting the output terminal of a continuous direct current generator or pulsed direct current generator to a first or working electrode composed of a metal plate or other conductive substances covered with a moistened pad of porous material impregnated with an aqueous solution of ionic drug and a second or counter electrode structured similar to the first electrode but not soaked with the drug. From the above, it is clear that actual application of iontophoresis through these prior art techniques is very difficult, and while iontophoresis is a very effective method for drug application, this difficulty in application has prevented its use from becoming widespread.

Furthermore, the iontophoresis is generally applied to the human skin by using a continuous or pulsed direct current having the same polarity as that of the drug to be applied. However, the human skin S has ohmic resistance $R_{dc}$ and a polarization impedance Z comprising (i) polarization resistance $R_{pol}$ and (ii) polarization capacity $C_{pol}$, as shown in FIG. 1, which illustrates a skin equivalent circuit diagram. For example, where conventional iontophoresis utilizes a continuous direct current in which the ohmic resistance $R_{dc}$ is solely used as a current path, a high voltage must be applied to the human skin to introduce the necessary amount of the drugs for treatment since the ohmic resistance $R_{dc}$ is very high. The application of a high voltage to the human skin tends to strongly irritate the human skin, which causes burns and rubefaction in the skin. If a low voltage is applied to prevent these problems in the skin, the application of the necessary amount of the drugs becomes very difficult.

Furthermore, the ohmic resistance $R_{dc}$ of the human skin S has a value of approximately 10 kΩ·cm to 1 MΩ·cm, which does not depend upon the frequency of the electric source, whereas it is known in the art that the polarization impedance Z substantially converges to zero when the frequency of the electric voltage used is, for example, 10 kHz or more (Yamamoto et. al., Med. & Biol. Eng. & Comput., (1978), 16, 592–594; Yamamoto et. al., Japanese Journal of Medical Electronics and Biological Engineering (1973), 11, No. 5, 337–342).

Accordingly, when a voltage having a high frequency is applied to the human body, the iontophoresis can be carried out under a low voltage since the polarization impedance Z is decreased. However, the polarization impedance Z of the skin S forms a parallel circuit, together with the polarization resistance $R_{pol}$ and the polarization capacity $C_{pol}$, as shown in FIG. 1. For this reason, when a direct current pulse as shown in FIG. 2a is applied to the human skin, the electric current to be utilized in the introduction of the drugs is not substantially changed, compared with the case where a continuous direct current is applied as shown in FIG. 2b, because the polarization capacity is repeatedly charged and discharged and the charged residual charge (or polarization) is gradually but very slowly discharged (or depolarized) via the polarization resistance $R_{pol}$ during the no pulse output periods. Consequently, a decrease in the skin impedance cannot occur even when a direct current pulse having a high frequency is applied.

Furthermore, as shown in FIG. 2C, even when the output time period of the direct current pulse is shortened to cause residual charge (or polarization) due to the polarization capacity $C_{pol}$, it is expected that the skin impedance Z will be lowered by widening the intervals of the no pulse output period (i.e., decreasing the so-called duty ratio) to sufficiently decrease the electric current value. However, an improvement in the drug introduction efficiency is not expected because the residual charge (or polarization) is the charge remained on the skin, which is not concerned with the drug introduction.

SUMMARY OF THE INVENTION

Accordingly, an object of the present invention is to eliminate the above-mentioned problems in the prior arts by providing an iontophoresis device capable of sufficiently decreasing the skin impedance, thereby allowing the iontophoresis device to be used under a low voltage and a high electric current and, furthermore, permitting the iontophoresis device to be safely applied to the human skin under a high voltage without causing undesirable irritation in the skin, especially without causing burns and rubefaction in the skin.

Another object of the present invention is to provide an iontophoresis device having a light weight and capable of direct and very easy application to the patient's skin by a simple operation and over a long period of time.

Other objects and advantages of the present invention will be apparent from the description set forth hereinbelow.

In accordance with the present invention, there is provided an iontophoresis device comprising:
 (a) an electric source;
 (b) a pulse generator
 (c) a working electrode;
 (d) a counter electrode; and
 (e) a means for effecting depolarization between the above-mentioned electrodes during the period in which a therapeutic pulse stops (i.e., a means for discharging the charges accumulated in said electrodes during each intermission period of therapeutic pulses generated by said pulse generator (b)).

BRIEF DESCRIPTION OF THE DRAWINGS

The present invention will be better understood from the description set forth below with reference to the drawings in which:

FIGS. 2a, 2b, and 2c are typical waveform diagrams of the conventional iontophoresis, wherein FIG. 2a is a waveform diagram of the pulse voltage; FIG. 2b is a waveform diagram of the electric current flowing in the human body when the pulse has the waveform of FIG. 2a; and FIG. 2c is a waveform diagram of the current when the pulse having the decreased duty ratio of the pulse (a) is applied;

FIGS. 4a and 4b are waveform diagrams of the first embodiment of the present iontophoresis device of FIG. 3, wherein FIG. 4a is a waveform diagram of the pulse voltage and FIG. 4b is a waveform diagram of the current passing through the human body when the pulse having the waveform of FIG. 4a is applied;

FIGS. 6a and 6b are waveform diagrams of the device shown in FIG. 5, wherein FIG. 6a is a waveform diagram of the pulse voltage and FIG. 6b is a waveform diagram of the current passing through the human body when the pulse having the waveform of FIG. 6a is applied;

FIGS. 7 to 10 illustrate a more specified embodiment of the present iontophoresis device, wherein FIG. 7 is a block diagram thereof; FIG. 8 is a circuit diagram illustrating the pulse generating circuit and voltage converter circuit; FIG. 9 is a circuit diagram illustrating the output current limiting circuit and switch mechanism.

FIGS. 11 to 13 illustrate another specified embodiment of the present iontophoresis device, in which the residual charge can be recovered, wherein FIG. 11 is the block diagram thereof; FIG. 12 is a closed circuit diagram when the output therapeutic pulse is generated; and FIG. 13 is a closed circuit diagram when the output therapeutic pulse is stopped;

FIGS. 16 and 17 illustrate a structure of the first embodiment of the present iontophoresis device, wherein FIG. 16 is a cross-sectional view thereof, taken along the line X—X of FIG. 17, and FIG. 17 is a bottom plan view thereof;

FIGS. 18 and 19 illustrate a structure of the second embodiment of the present iontophoresis device, wherein FIG. 18 is a cross-sectional view thereof, taken along the line Y—Y of FIG. 19, and FIG. 19 is a perspective view thereof; and FIGS. 20 and 21 illustrate structures of the third and fourth embodiments of the present iontophoresis device, wherein FIG. 20 is a cross-sectional view of the third embodiment, and FIG. 21 is a perspective view of the fourth embodiment.

DESCRIPTION OF THE PREFERRED EMBODIMENTS

Figure 3:
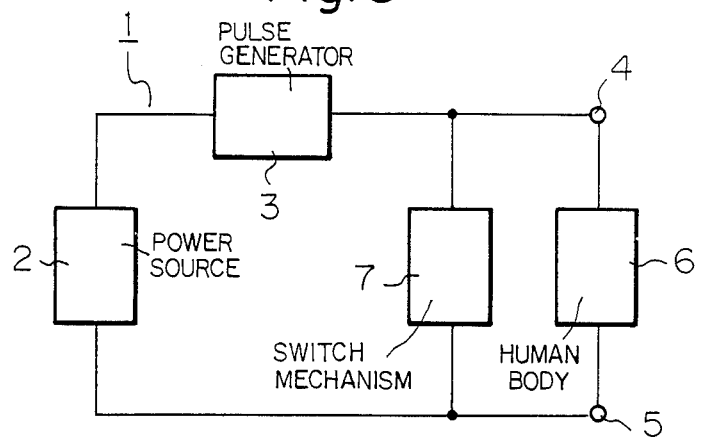
FIG. 3 is a block diagram illustrating a first embodiment of the present iontophoresis device.
Figure 4A:
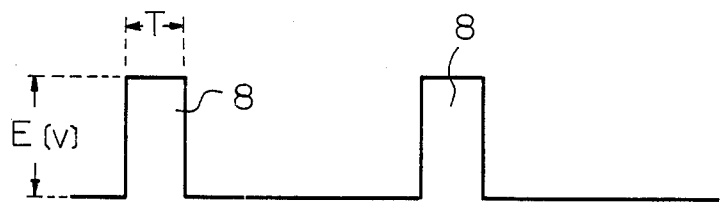
Figure 4B:
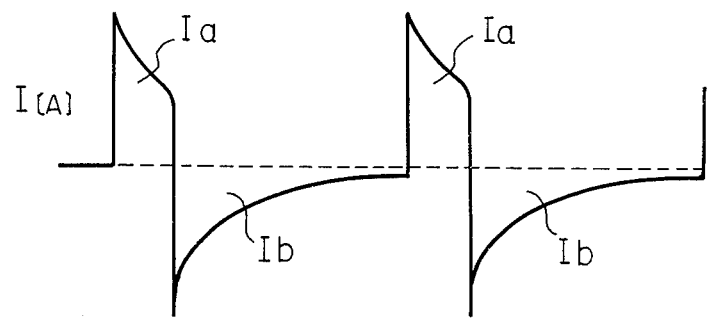

Referring to FIGS. 3 and 4 illustrating a first embodiment of the present iontophoresis device, the iontophoresis device 1, shown as a block diagram in FIG. 3, comprises a power source 2 (e.g., a dry element battery having a voltage of 6V), a pulse generator 3 capable of generating a direct current pulse having a frequency of about 50 kHz as shown in FIG. 4a, a working electrode 4 containing an ionic agent, a counter electrode 5, a human body 6 connected to the working and counter electrodes 4 and 5, and a switch mechanism 7. The switch mechanism 7 is provided, in parallel to the human body 6, for depolarizing the polarized potentials of the electrodes 4 and 5, preferably for bringing the polarized potentials of the electrodes 4 and 5 to an equal level simultaneously with the stoppage of the therapeutic pulses 8, 8, ... generated from the pulse generator 3. That is, according to this mechanism, the residual charge (i.e., polarization) charged in the polarization capacity Cpol of polarization impedance Z of the skin S is discharged or depolarized by shortcircuiting the electrodes 4 and 5. When this structure is applied to the human body 6, the current passing through the human body is as shown in FIG. 4b. That is, during output time period T of the therapeutic pulse shown in FIG. 4a, the current (i.e., pulse current Ia) flows mainly to the polarization impedance Z of the skin S of the human body 6, and the ionic agent contained in the working electrode 4 is mainly endermically absorbed via the polarization resistance Rpol of the skin S. Simultaneously when the treatment pulses 8, 8, ... are stopped, the working electrode 4 and the counter electrode 5 are short-circuited by the switch mechanism 7 and, therefore, the residual charge (i.e., polarization) charged in the polarization capacity Cpol of the polarization impedance Z of the skin S of the human body 6 during the output period of the therapeutic pulses 8 is discharged or depolarized as a depolarization current Ib during the period when the therapeutic pulses are stopped. Thus, the electric potentials of the both electrodes are lowered to the predetermined level or less, preferably to an approximately equal level.

Figure 5:
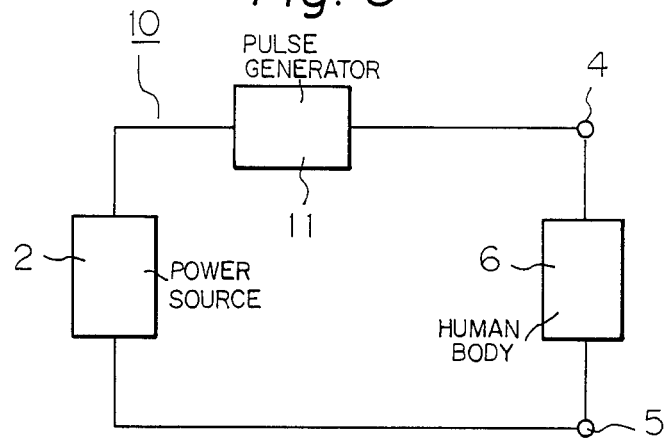
FIG. 5 is a block diagram illustrating a second embodiment of the present iontophoresis device.
Figure 6A:
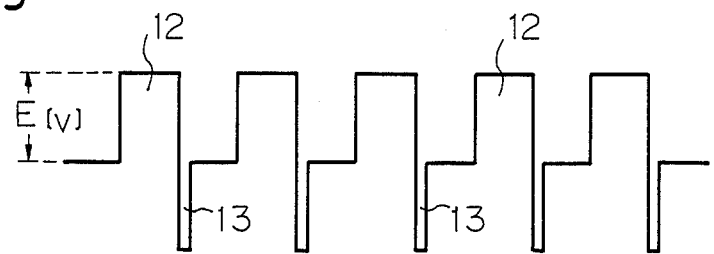
Figure 6B:
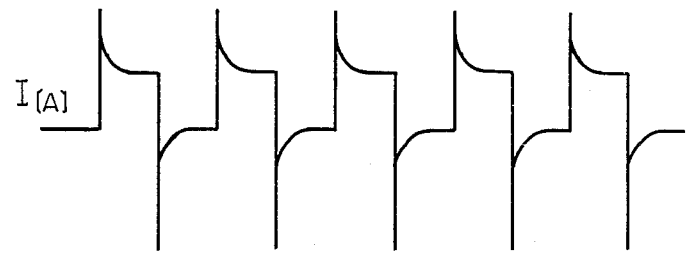
Figure 7:
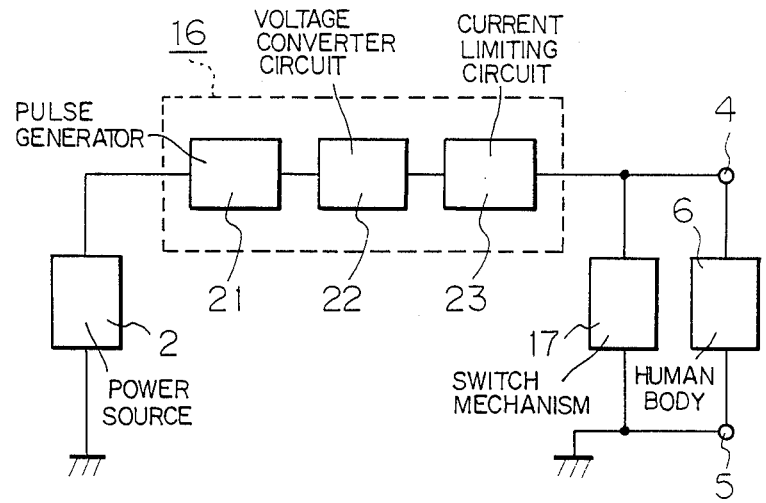
Figure 8:
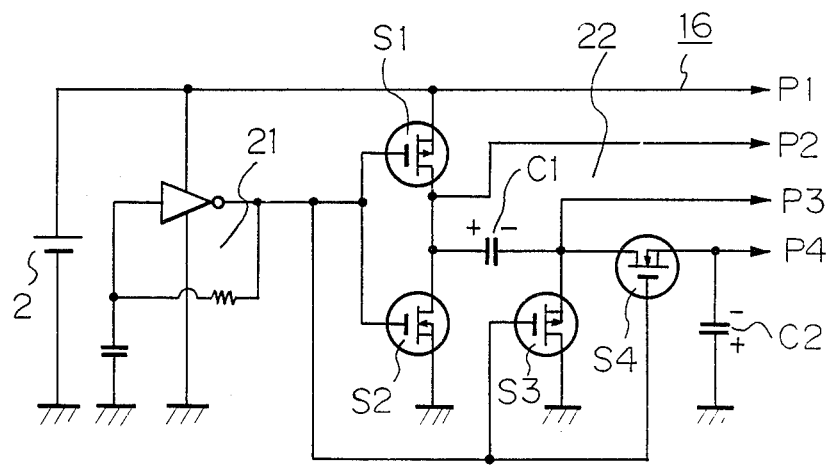
Figure 9:
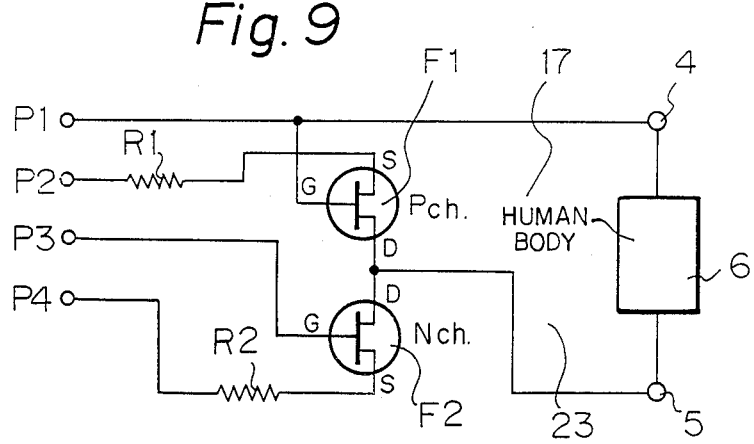

Referring to FIGS. 5 and 6, illustrating a second embodiment of the present iontophoresis device, the iontophoresis device 10, shown as a block diagram in FIG. 5, comprises a power source 2 (e.g., a dry element battery having a voltage of 6V), a working electrode 4 containing an ionic agent, a counter electrode 5, a human body 6 connected to the working and counter electrodes 4 and 5, and a pulse generator 11. The pulse generator 11 is formed in such a manner that the pulse generator 11 generates therapeutic pulses 12, 12, ... having, for example, a frequency of approximately 100 kHz as shown in FIG. 6a, while it generates pulse components 13, 13, 13, ... in the reverse direction of the therapeutic pulses to effect depolarization between the electrodes 4 and 5 simultaneously with the stoppage of the therapeutic pulses 12, 12, ... The reverse pulse components 13, 13, 13, ... are forced to discharge or depolarize the residual charge stored in the skin S of the human body 6 connected to the both electrodes 4 and 5 during the output period of the therapeutic pulses 12, 12, ... simultaneously with the stoppage of the pulses 12, 12, ... Thus, the current as shown in FIG. 6b flows through the skin S of the human body 6.

Although it has been explained in the above embodiment shown in FIGS. 5 and 6 that only one pulse generator generates both the therapeutic pulse and the forced discharge pulse components, it should be noted that each pulse can be also separately generated from different pulse generators and can be applied to the human body after turning both pulses. Furthermore, the present iontophoresis device may also include a mechanism for optionally or automatically controlling the time interval and the voltage of the forced discharge pulse components to effect the depolarization between the working and counter electrodes.

Furthermore, it has been explained in the above-mentioned embodiments that the switch mechanism is provided for effecting the depolarization between the working and counter electrodes and that the pulse generator is provided for generating the reverse pulse components. However, it should be noted that any means capable of effecting similar functions can be also used in the present invention.

Furthermore, although various factors such as a power source voltage, pulse width, and generating frequency of the pulse can be varied in a wide range, depending upon, for example, the characteristics of the drugs to be applied and the intended use, it is generally preferred that the duty ratio is 0.1 to 0.7, more preferably 0.1 to 0.4, and the frequency is 1 kHz to 500 kHz, more preferably 5 kHz to 200 kHz.

The extent of the depolarization effected in the present invention is such that the residual polarization voltage constantly applied to the human skin does not cause skin irritation. Although such a polarization voltage can be optionally determined depending upon various operating conditions such as the pulse voltage to be used, the preferable residual voltage is 3V or less, more preferably 1.5V or less. This value can be represented in terms of a ratio of the depolarization current value to the pulse current value by about 50% or more, preferably 60% or more, and more preferably 70% or more. From another point of view, the depolarization current value is preferably a constant value close to a zero level.

On the other hand, it is clear that a constant bias voltage can be further applied, in addition to the pulse voltage, within such a range that no skin irritation is caused. That is, the pulse iontophoresis and minute continuous direct current may be used together within the above-mentioned range.

Although the general embodiment of the human skin equivalent circuit diagram has been explained, a similar explanation can be effective even where the electric characteristics of the electrodes are taken into consideration.

As is clear from the above-explanation, according to the present iontophoresis device, the current flowing through the human skin is about a dozen to several dozens times those where the continuous direct current or pulsed direct current are applied at the same electric source voltage. This means that several to several dozens times the ionic agent introduction effect can be obtained, although the loss of the electric current stored in the polarization capacity Cpol (i.e., polarization loss) and the intermission period of the therapeutic pulses must be taken into consideration. Furthermore, according to the present invention, the iontophoresis device capable of introducing the necessary amount of drugs under a low voltage or even under a high voltage (e.g., 50V) with an extremely weak irritation effect on the human skin, without causing burns and rubefaction in the skin and also capable of being used over a long period of time, can be obtained.

Especially as shown in the second embodiment, when the pulse components in the reverse direction of the therapeutic pulse are generated simultaneously with the stoppage of the therapeutic pulse, the effect of the above-mentioned time constant due to, for example, the resistance components of the circuit, becomes very low. For this reason, the direct current pulse having a high frequency can be used since the depolarization between both electrodes can be effected simultaneously with the stoppage of the therapeutic pulse. As a result, the desired iontophoresis can be conducted with a lower skin impedance.

Although it has been explained from the practical point of view that the periodic pulse is used in the present iontophoresis device, it should be noted that a non-periodic pulse can be also used in the present invention. It should be also noted that the pulse waveform is not essentially limited to a rectangular wave.

The constituent elements and application embodiments of the present iontophoresis device will now be explained in detail hereinbelow.

FIGS. 7 to 10 illustrate one example of the circuit of the iontophoresis device in which a pulse generating mechanism 16 is provided with a charge pump type voltage converter circuit for increasing the voltage of the electric source 2 and an output current controlling circuit for controlling the output current.

The pulse generating mechanism 16 comprises a pulse generator 21, a charge pump type voltage converter circuit 22 for increasing the output voltage of the pulse, and an output current controlling circuit 23. As explained above, the reference numerals 4 and 5 represent the working and counter electrodes, respectively, and the reference numeral 6 represents a human body connected to both electrodes. The numeral 17 represent a switch mechanism.

More specifically, the electric source 2, which is, for example, a button shaped small and light weight lithium battery having an output of 3V, is connected to the pulse generator 21 of the pulse generating mechanism 16. The pulse generator 21 is then connected to the charge pump type voltage converter circuit 22 for increasing the voltage of the electric source to approximately twice the original voltage. The charge pump type voltage converter circuit 22 is composed of, for example, switching elements S1, S2, S3, and S4 in which FET is used, a charge pump capacitor C1, and a charge reserve capacitor C2. The output terminals P1, P2, P3, and P4 of the charge pump type voltage converter circuit 22 are connected to a current limiting circuit 23 and a switch mechanism 17. The current limiting circuit 23 is composed of a resistance R1, an FET F1, a resistance R2, and an FET R2. The switch mechanism 17 is composed of FETs F1 and F2, which are controlled by the outputs derived from the output terminals P2 and P3 of the above-mentioned charge pump type voltage converter circuit 22.

The action and operation of the circuit thus formed will now be explained. The continuous direct current having an output of 3V discharged from the electric source 2 is first transformed (or converted) to a direct pulse, shown in FIG. 10a, by the pulse generator 21. The direct pulse a thus transformed is then transformed, by the charge pump type voltage converter circuit 22, to a therapeutic pulse 20 (i.e., doubled voltage direct current pulse) shown in FIG. 10b. That is, when the first half cycle T1 of the direct current pulse a is generated, the charge pump capacitor C1 is charged in the polarity shown in FIG. 8 because the switching elements S1 and S3 are continued. When the next half cycle T2 of the direct current pulse is generated, the switching elements S2 and S4 are continued and the switching elements S1 and S3 are open. As a result, the full charge of the capacitor C1 is transferred to the charge reserve capacitor C2. Thus, the polarity becomes negative against the ground and the electric potential between the output terminal P1 and P4 is increased to 6V, which is approximately twice the voltage of the electric source.

Figure 10A:
FIG. 10a is a waveform diagram of the pulse voltage.
Figure 10B:
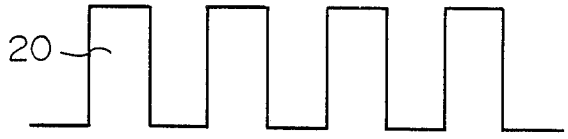
FIG. 10b is a voltage waveform diagram of the therapeutic pulse.
Figure 10C:
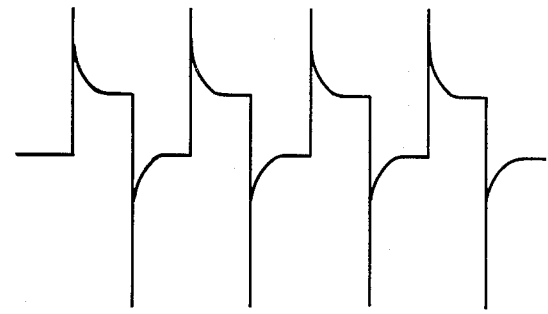
FIG. 10c is a waveform diagram of the current passing through the human skin.
Figure 10D:
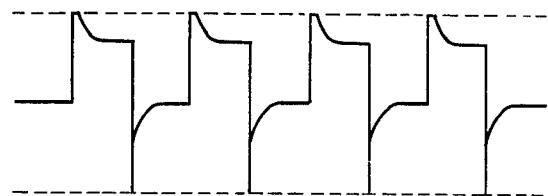
FIG. 10d is a waveform diagram of the current of which waveform is shaped by a output current controlling circuit.

The therapeutic pulse 20 thus increased is discharged to the working electrode 4 and the counter electrode 5 via the current limiting circuit 23 and the switch mechanism 17, and then applied to the human body 6. In this case, the source and the drain of the FET F1 of the switch mechanism 17 are continued when the therapeutic pulse 20 is generated and, therefore, as electric potential difference occurs between the working electrode 4 and the counter electrode (5). Thus, the ionic drug contained in the working electrode (4) is introduced into the human body 6. On the other hand, when the therapeutic pulse 20 is stopped, the source and drain of the FET F2 of the switch mechanism 17 are continued by the output signal from the output terminal P2, while the FET F2 becomes open by the output signal from the output terminal P3. Accordingly, the residual charge (i.e., polarization) stored in the skin S of the human body 6 is short-circuit discharged (or depolarized) and the current as shown in FIG. 10c passes through the human body 6. As is clear from the current waveform of FIG. 10c, when the direct current pulse is applied to the human body, large peak currents flow therethrough because the impedance is very low at the leading and trailing edges of the waveform. However, these peak currents can be limited by the function of the output current limiting circuit 23 in the present iontophoresis device. As a result, the upper and lower peak currents passing through the human body can be cut as shown in FIG. 10d.

It has been explained in the above-mentioned embodiment that the switch mechanism for effecting the depolarization between the working and counter electrodes during the stoppage of the therapeutic pulse and the pulse generating mechanism provided with the charge pump type voltage converter circuit and the current limiting circuit are used. However, the voltage converter circuit and the output current limiting circuit can be also combined with a circuit that generates the pulse component in the reverse direction of the therapeutic pulse simultaneously with the stoppage of the therapeutic pulse to effect the depolarization between the working and counter electrode, as previously mentioned. Furthermore, either or both of the voltage converter circuit and the current limiting circuit may be optionally deleted from the present iontophoresis device.

Furthermore, although the charge pump type voltage converter circuit is used in the above-mentioned embodiment as one example of the voltage converter mechanism of the voltage of the electric source, it should be noted that any other mechanism having the same function, such as a voltage converter based on a transformer or DC-DC converter may be used in the present invention. In addition, although the charge pump type boosting is used at one stage, in the above-mentioned embodiment, for obtaining approximately twice the initial voltage, the charge type boosting can be optionally used at multi stages for obtaining any desired voltage. Furthermore, although the current limiting circuit and the switch mechanism are explained as an integral form in the above embodiment, these can be used separately or any other mechanisms having the same function can be also used in the present invention. It should be noted that the pulse generator and the switch mechanism are not limited to those specifically illustrated in the above embodiment.

As is clear from the above description, the desired beneficial treatment effect can be obtained even by using an electric source having a low voltage, since the voltage converter mechanism is provided in the pulse generating mechanism according to the present iontophoresis device.

Especially when the button type battery having an output of several volts or less and the charge pump type voltage converter circuit are used as shown in the above embodiment, an extremely preferable circuit for a plaster type iontophoresis device suitable for use in direct adhesion application to the human skin as a whole can be obtained since the total volume of the device can be minimized.

Furthermore, according to the above-mentioned embodiment of the present iontophoresis device, the large peak currents at the leading and trailing edges of the therapeutic peak can be effectively limited and, therefore, the amounts of the drugs to be introduced into the human body can be controlled. Furthermore, the desired controlled delivery of the drugs not depending upon individual impedance can be attained by freely controlling the output current when a variable resistance circuit, variable duty ratio circuit or frequency converting circuit is inserted into the output current limiting circuit.

The first example explained above is formed such that the residual charge stored in the polarization capacity of the skin is depolarized by short-circuiting the charge or by applying the reverse pulse components to the charge. As the second example, the iontophoresis device, in which the above-mentioned residual charge is depolarized and simultaneously and effectively recovered to obtain a low electric power consumption type device, will be further explained in detail hereinbelow referring to FIGS. 11 to 13.

Figure 11:
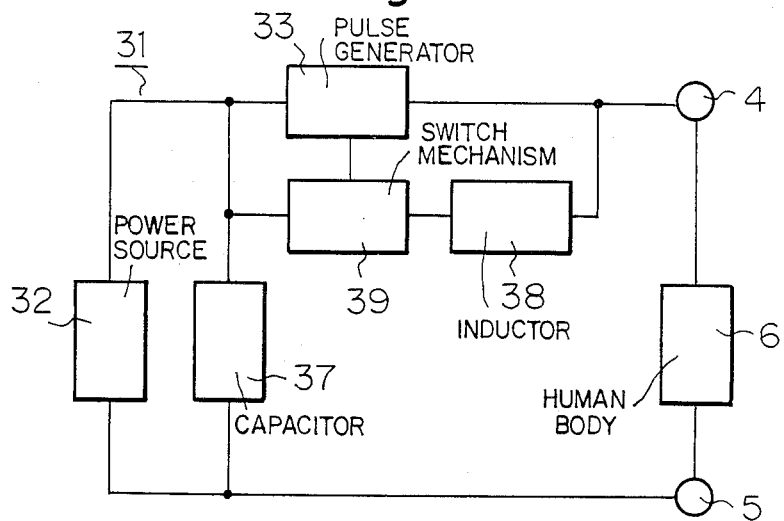

The iontophoresis device 31, shown in a block diagram of FIG. 11, comprises a power source 32 (e.g., a day element battery having a voltage of 6V), a pulse generator 33 capable of generating a direct current pulse having a frequency of about 50 kHz as shown in FIG. 4a, a working electrode 4 containing an ionic agent, a counter electrode 5, a human body 6 connected to the working and counter electrodes 4 and 5, a capacitor 37 for recovering the residual charge, which is connected in parallel to the electric source 32, and an inductor 38, which is connected to a switch mechanism 39. The switch mechanism 39 is provided for forming a closed circuit for recovering the residual charge shown in FIG. 13 (i.e., a closed circuit in which the inductor 38 is connected in series to both electrodes 4 and 5), simultaneously with the stoppage of the therapeutic pulses 8, 8, ... generated from the pulse generator 33. The switch mechanism 39 is connected in parallel to the pulse generator 33.

Figure 12:
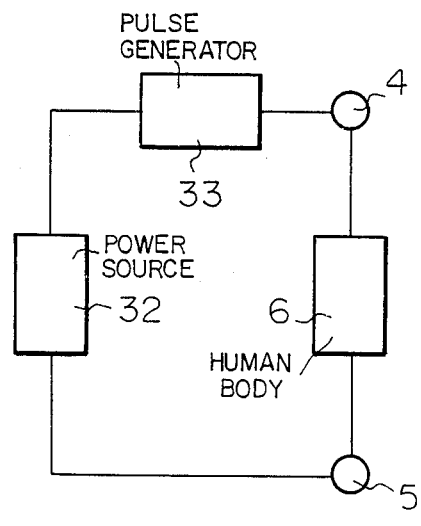
Figure 13:
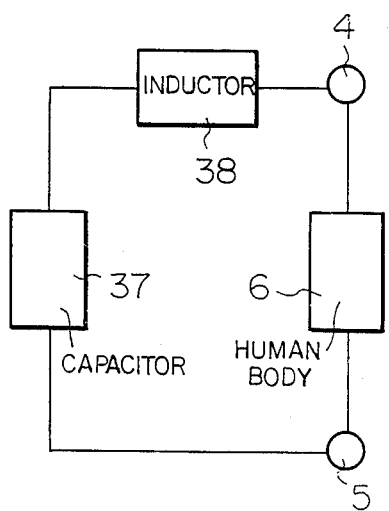

The iontophoresis device shown in FIGS. 11 to 14 can be used as follows. That is, the working and counter electrodes 4 and 5 are first adhered to the human body 6. Thus, the drug introduction circuit shown in FIG. 12 is formed. That is, the pulse generator generates the pulse 8 shown in FIG. 4a. As a result, during the output time T of the pulse, the current (i.e., pulse current Ia) flows mainly through the polarization impedance Z of the skin S of the human body 6 and, therefore, the ionic drug contained in the working electrode 4 is endermically absorbed mainly via the polarization resistance Rpol of the skin S. Simultaneously with the stoppage of the therapeutic pulse 8 (i.e., the pulse generator 33 is in an OFF position), the switch mechanism 39 turns on, whereby the circuit for recovering the residual charge is formed as shown in FIG. 13. This circuit allows the recovery of the residual charge stored in the polarization capacity Cpol of the polarization impedance Z of the skin S of the human body 6 while the therapeutic pulse is being generated. The residual charge is recovered in the capacitor 37 for recovering the residual charge by the L-C resonance between the polarization capacity Cpol and the inductor 38. The charge thus recovered is discharged in the next cycle at which the therapeutic pulse 8 is generated. Furthermore, this residual charge recovery action allows the lowering of the electric potential between both electrodes to the given value, preferably to equal levels, by discharging (or depolarizing) the residual charge (i.e., polarization) stored in the polarization capacity (i.e., depolarization current Ia) during the stoppage of the therapeutic pulse 8.

Although it is explained in the above example that the L-C resonance is used as a means for simultaneously depolarizing and recovering the residual charge, it should be noted that the present invention is not limited to this embodiment. For example, a capacitor only can be provided for recovering the residual charge. Furthermore, any other means capable of recovering the residual charge, for example, a means based on R-C resonance, can also be used in the present invention.

As is clear from the above description, according to this example of the present iontophoresis device, the electric power consumption necessary for the treatment can be effectively decreased since the extra residual charge, which is stored in the polarization capacity of the human skin and which is not concerned with the drug introduction to the human skin, can be extremely effectively recovered and reused, while the residual charge is depolarized. Furthermore, the small sized and light weight device can be effectively formed since the desired drug introduction can be effected by using a relatively small capacity and small sized battery.

The constituent elements and their operation of the example capable of recovering the residual charge will now be explained hereinbelow.

Figure 14:
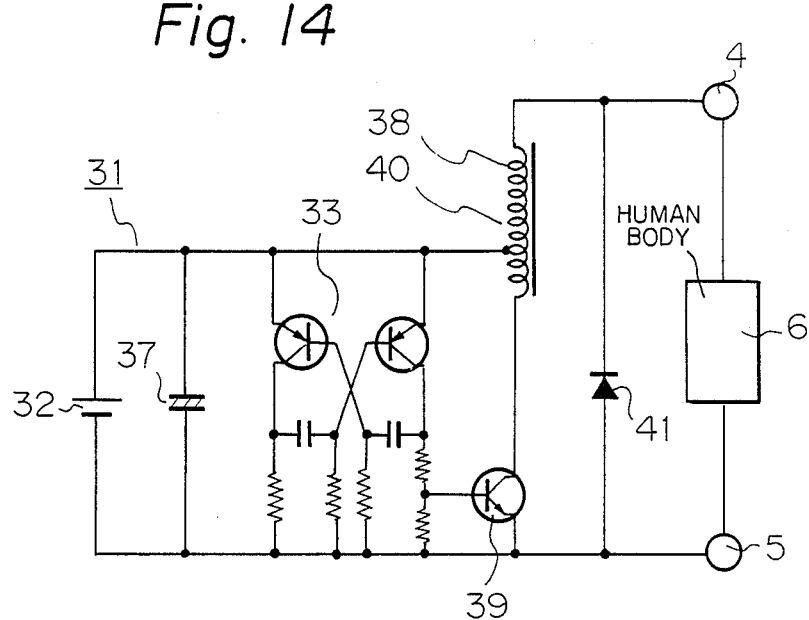
FIGS. 14 and 15 are circuit diagrams more specifically illustrating embodiments of the present iontophoresis device.

FIG. 14 illustrates one example of the circuit diagram for simultaneously depolarizing and recovering the residual charge in the load capacity by the L-C resonance between an inductor and the load capacity, in which a transformer for boosting the pulse voltage is provided and the secondary winding of the transformer is utilized as the inductor. In FIG. 14, the reference numeral 32 represents an electric source, which can be, for example, a button shaped small sized and light weight lithium battery having an output of 3V, for obtaining a small-sized and light weight device. The electric source 32 is connected to the pulse generator 33. The pulse generator 33 is formed by, for example, a free running multivibrator circuit, so that pulse having a frequency of 50 KHz and a duty ratio of 0.2 is generated. A transformer 40 is provided for boosting the pulse voltage and is formed in a winding ratio of, for example, 1:3. The secondary winding of the transformer 40 is formed so as to function as the inductor 38 for the L-C resonance. A switching transistor 39 is provided for turning on and off the primary winding of the transformer 40 by the output from the pulse generator 33. The reference numerals 41 and 37 represent a diode for protecting the circuit and a capacitor for recovering the residual charge respectively. The working and counter electrodes 4 and 5 are connected to the human body 6. This example of the present invention can function in the same manner as the previously explained example and have the same effects.

Figure 15:
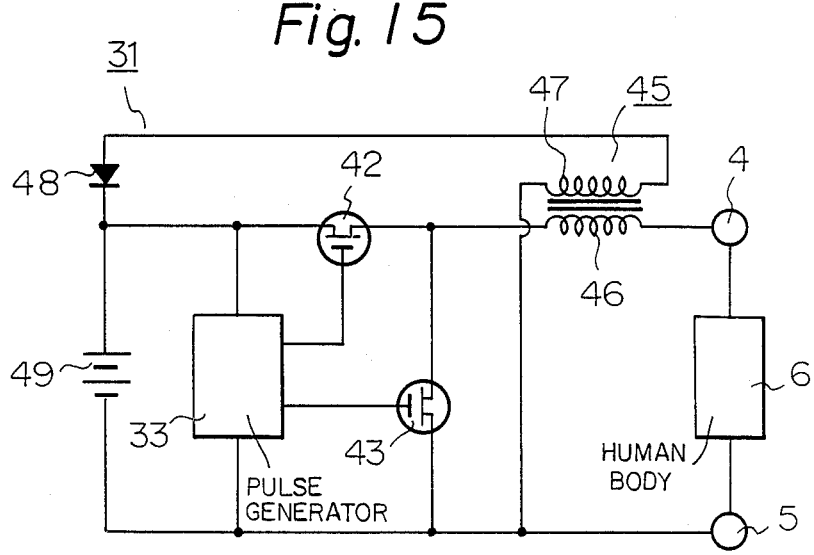

FIG. 15 illustrates a circuit diagram of another example for simultaneously depolarizing and recovering the residual charge in the load capacity by a function of an induced current inducing type transformer 45. The primary winding 46 of the transformer 45 is connected in series to both electrodes 4 and 5 and the secondary winding 47 is connected, through a diode 48 for preventing inverse current, to a rechargeable battery 49. A pulse generator 33 is connected to the rechargeable battery 49 and is also connected to the gates of the first and second FETs 42 and 43.

This circuit acts as follows. The pulse generator 33 generates a pulse 8 as shown in FIG. 4a by using the rechargeable battery 49 as an electric source. Simultaneously, at the leading edge of the pulse 8, the drain and the source of the FET 42 are continued. Accordingly, a current (i.e., pulse current Ia) flows mainly to the polarization impedance Z of the skin S of the human body 6 during the output time period T of the pulse 8 and the ionic drug contained in the working electrode 4 is endermically absorbed mainly through the polarization resistance Rpol of the skin S. Simultaneously when the pulse 8 is stopped, the FET 42 is turned off and the FET 43 is continued. Thus, the residual charge stored in the polarization capacity Cpol of the polarization impedance Z is instantaneously depolarized by a closed circuit including the primary winding 46 of the transformer 45, and an induced current is simultaneously induced in the secondary winding by the transformer 45. This induced current is effectively recovered, via the diode 48, in the rechargeable battery 49.

Although it has been explained in the above example that the residual charge is recovered in the rechargeable battery, this residual charge can be also recovered in the capacitor. Furthermore, the winding ratio of the transformer can be optionally changed, taking into consideration the induction efficiency of the induced current and the charging efficiency to the rechargeable battery or capacitor.

The entire structure of the present iontophoresis device will now be explained in detail.

Figure 16:
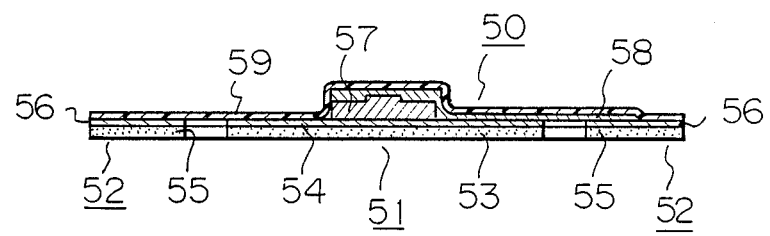
Figure 17:
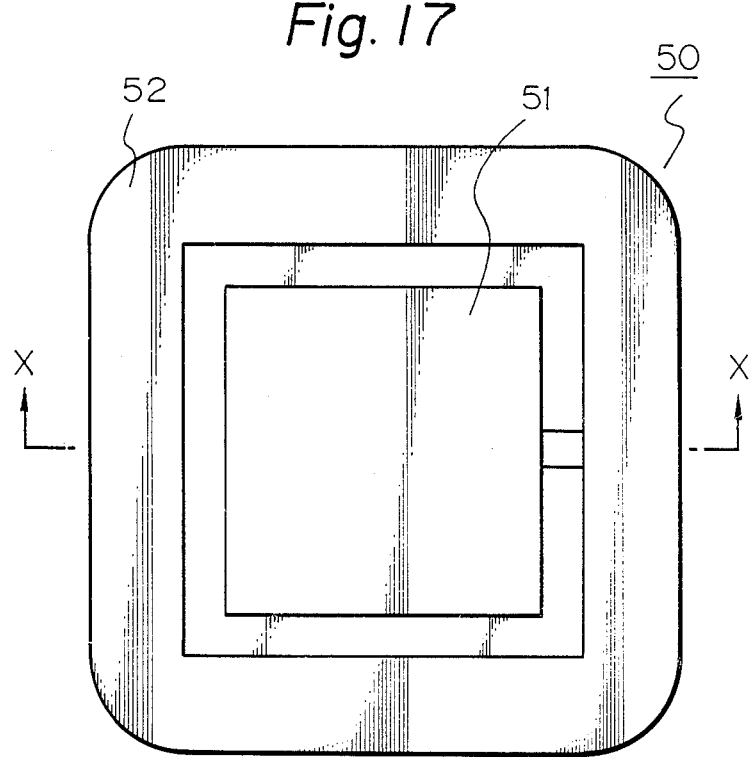

FIGS. 16 and 17 illustrate a first example of the present iontophoresis device. Referring to FIGS. 16 and 17, an iontophoresis device 50, which is in the form of a plaster (i.e., the entire device is adhered to the human skin), comprises a working electrode 51 and a counter electrode 52. The first electrode 51 is formed by laminating a conductive gel layer 53 containing an ionic agent in the form of a flexible sheet or film with a current-distribution conductive member layer 5, which layer is formed by a metallic foil (e.g., an aluminum foil), a conductive rubber or resin film, carbon film, or conductive coating. The second electrode 52 is formed by laminating a conductive gel layer 55 in the form of a flexible sheet or film with a current-distribution conductive member layer 54 as in the working electrode. A power supply unit 57 is mounted in the approximately center portion of the upper surface of the working electrode 51. The power supply unit 57 comprises an electric source (e.g., a button battery), a pulse generator, a means for bringing the electric potential of both electrodes 51 and 52 to an approximately equal level while the therapeutic pulse is stopped, and a means for recovering the residual charge. The one output terminal (e.g., negative (−) terminal) of the power supply unit 57 is in contact with the current-distribution conductive member layer 54. On the other hand, the other output terminal (e.g., positive (+) terminal) of the power supply unit is connected to the current-distribution member layer 56 of the counter electrode 52 by means of, for example, a lead wire 58 made of an aluminum foil which is applied on the bottom surface except for both end portions by an insulating coating. The working and counter electrodes 51 and 52 are separately fixed at a spaced distance by an insulating backing layer 59, which is in the form of a flexible sheet or film of a non-conductive synthetic resin. Thus, the working electrode 51, the counter electrode 52, and the power supply unit 57 are integrally structured by means of the insulating backing layer 59.

The present iontophoresis device thus formed can be applied by adhering the device to the human skin in such a manner that the working electrode 51 is in contact with the intended portion of the human body to be treated. Thus, electrodes 51 and 52 form a closed circuit through the human body, thereby promoting the penetration or absorption of the ionic agent contained in conductive gel layer 53 of the working electrode 51 through the skin. According to this example of the present iontophoresis device, the iontophoresis device having a light weight and being capable of very easy and direct application to the human skin, and giving a sample operation and effective drug introduction effect can be obtained.

Referring to FIGS. 18 and 19 illustrating the second example of the present iontophoresis device, an iontophoresis device 60 comprises a working electrode 61 and a counter electrode 62. The electron-distribution conductive member layers 63 and 64 of the working and counter electrodes 61 and 62 are separated from each other at a distance of approximately 5 mm. An ionic agent-containing conductive gel layer 65 having a very thin thickness (e.g., approximately 0.3 mm) is adhered to the bottom surfaces of the electrodes 61 and 62. Furthermore, the working and counter electrodes 61 and 62 are separately fixed and integrally supported on an insulating backing layer 66. The reference numerals 67 and 68 represent terminals connected to the working and counter electrodes 61 and 62, respectively. The top portions of the terminals 67 and 68 are projected through the insulating backing layer 66. A power supply unit 69 is electrically and mechanically connected to the terminals 67 and 68.

This example of the present iontophoresis device can be applied in the same manner as in the first example mentioned above. According to this example, since the same conductive gel layer (i.e., only one conductive gel layer 65 containing an ionic agent) is adhered to the current-distribution conductive member layers 63 and 64 of the working and counter electrodes 61 and 62, some leak current occurs between each electrode. However, since the conductive gel layer itself possesses some resistance, and since the distance between the conductive member layers 63 and 64 is much larger than the thickness of the conductive gel layer 65, the penetration effect of the ionic agent into the skin is not substantially affected.

According to this example, in addition to the advantages of the first example mentioned above, there is a further advantage in that the production of the iontophoresis device can be very simply and effectively conducted. That is, the desired iontophoresis device can be readily produced by cutting a strip sheet, on which a conductive gel layer, a conductive member layer, and an insulating backing layer are laminated, at a predetermined distance, followed by placing the terminals and the power supply. In particular, this production process is very advantageous especially for mass production of the device. Furthermore, when the spaced distance between both terminals is narrowed, and when the power supply is placed in the approximate center portion of the upper surface of the device, as in the second example mentioned above, the effect due to the size of the power supply in the entire device can be minimized and the adhesion of the device to the human body even at a curved portion can be smoothly carried out without impairing the flexibility of the device.

The third examples of the present iontophoresis device will now be explained with reference to FIG. 20.

Figure 20:
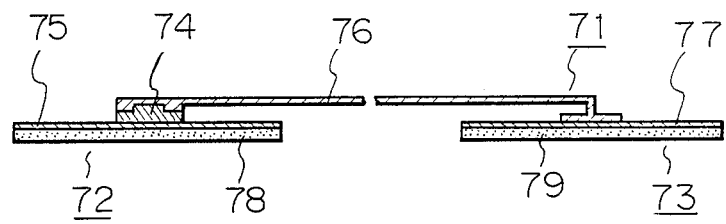

Referring to FIG. 20, an iontophoresis device 71 comprises a working electrode 72, a counter electrode 73, and a power supply unit 74. The negative (−) terminal of the power supply unit 74 is connected to the current-distribution conductive member layer 75 of the working electrode 72 and the positive (+) terminal is connected, via a lead wire 76, to an electric-distribution conductive member layer 77 of the counter electrode 73.

This example of the present iontophoresis device enables the working electrode to be applied to the body separated from the counter electrode at a distance, limited only by the length of the lead wire. Thus, the iontophoresis device can be easily applied to the intended portion of patient even when the portion is very small or has a relatively large curvature radius. Furthermore, when a large amount of perspiration is extruded onto the skin, especially at a high temperature and high humidity, the iontophoresis device is not affected by the electric current flowing on the surface of the skin during application since the two electrodes are separately placed.

The fourth examples of the present invention will now be explained with reference to FIG. 21.

Figure 21:
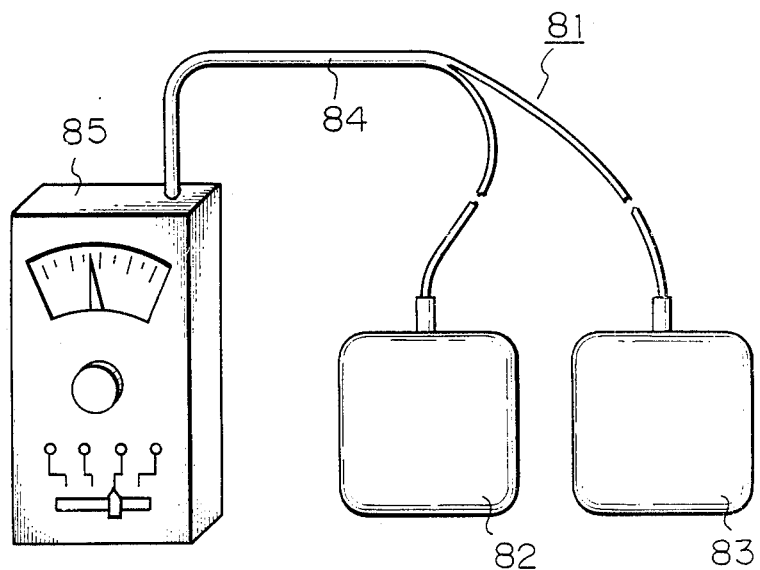

Referring to FIG. 21, an iontophoresis device 81 comprises a working electrode 82, a counter electrode 83, and a power supply unit 85. The power supply unit is connected, via a lead wire 84, to the working and counter electrodes 82 and 83. The power supply unit 85 includes an electric source (e.g., four UM-3 (JIS) type dry element batteries), a pulse generator utilizing a transformer, a switch mechanism for bringing the electric potentials of both electrodes 82 and 83 into substantially the equal level during the stoppage of the therapeutic pulse, and a means for recovering the residual charge. Furthermore, the power supply unit 85 is provided with an output current variable circuit and a timer circuit.

According to this example, since the power supply unit is not integrally placed with both electrodes, a large capacity of the dry element battery can be used since fact there is enough room in the circuit space. Furthermore, since the working and counter electrodes can be composed of an extremely lightweight thin sheet in the form of a simple film, the adhesion of the electrodes to the human skin can be extremely facilitated. The use of the output current variable circuit provided at the power supply unit can optionally control the output current amount, depending upon the skin resistance of a patient, the kind of drug to be introduced, and the necessary amount of a drug to be introduced. Furthermore, the use of the timer circuit in the power supply unit can effectively prevent undesirable over application of a drug into the human body.

Although it has been explained hereinabove that the conductive gel containing an ionic agent is used in the working electrode, it should be noted that various other materials capable of retaining the impregnated ionic agent or electrolyte therein can be also used. Examples of such materials are paper materials such as a water-absorbent paper, fabric materials such as a gauze, fiber materials such as absorbent wadding, sponge or porous materials such as open-cell type synthetic resin foams or water-absorbent resin. Furthermore, although the ionic agent is already contained in the conductive gel layer of the working electrode in the above-mentioned examples of the present iontophoresis device, the ionic agent can be applied to the working electrode and/or the skin at the time when the iontophoresis device is applied to the human body. That is, when the iontophoresis device having a conductive layer which does not contain an ionic agent is applied to the human skin, an ionic agent contained in, for example, an ointment or cream can be applied to the working electrode or the intended portion of the skin and, then, the iontophoresis device is applied to the human skin. Furthermore, a polarity switching means can be provided in the iontophoresis device in such a manner that the negative or positive polarity can be freely changed depending upon the polarity of the effective drug ion.

Furthermore, when the physical conditions of the patient are changed depending upon the drug introduction amount, or when the drug introduction amount must be controlled depending upon the physical conditions of the patient, a feedback mechanism can be provided in the iontophoresis device in such a manner that the output current is automatically controlled by monitoring the physical conditions of the patient. For example, when the drug introduction amount must be controlled depending upon a blood sugar value in the blood of the patient in the case of insulin administration, a sensor for monitoring the blood sugar value in the blood can be advantageously connected to the power supply unit so that a feedback mechanism for controlling the output current and/or output time is operated by detecting the output of the sensor. According to this construction, the most appropriate administration of a drug to the human body can be effected depending upon the physical conditions of the human body, which is by no means possible in the conventional methods.

The constituents of the iontophoresis device of the present invention will now be explained in detail hereinbelow.

Conductive gel layers

The conductive gel layers of the working and counter electrodes of the present iontophoresis device are composed of various hydrophilic natural or synthetic resins: for example, natural resinous polysaccharides such as karaya gum, tragacanth gum, and Xanthan gum; vinyl resins such as partially saponified polyvinyl alcohol, polyvinyl formal, polyvinyl methyl ether and copolymers thereof, polyvinyl pyrrolidone, and polyvinyl methacrylate; and acrylic resins such as polyacrylic acid and sodium salts thereof, polyacryl amide and partially hydrolyzed products thereof, partially saponified products of polyacrylic acid esters, and copoly (acrylic acid-arylamide). These hydrophilic natural or synthetic resins are softened and plasticized with water and/or polyols such as ethylene glycol, propylene glycol and glycerine and are molded to the form of a flexible sheet or film. The resultant gel layer has a shape retention property and good adhesiveness to the skin.

An ionic agent or drug is further included, or is to be included just before application to the skin, in the conductive gel layer of the working electrode, whereby the conductivity of the gel layer increases. If desired, a supporting electrolyte is optionally added to the gel layer as in the case of the so-called electrophoresis gel.

If desired or necessary, various electrolytes, such as sodium chloride, sodium carbonate, and potassium citrate, can be added to the conductive gel layer of the counter electrode to provide a sufficient conductivity. The electrolyte is usually added in an amount of about 1% to 15% by weight, based on the total weight of the gel layer.

The resultant conductive gel layers suitable for use in the present invention are in the form of a flexible sheet or film and can closely adhere to the skin. Therefore, the skin contact resistance is low. As a result, the ionic agent or drug effectively penetrates into the skin. Furthermore, it is advantageous from the viewpoint of practical application that the iontophoresis device can be directly applied to the intended skin without using an adhesive means such as a pressure-sensitive adhesive tape.

Especially when the above-mentioned natural resinous polysaccharides such as karaya gum are used as the basic material of the gel layers, gel layers having not only electrochemically good conductivity but also desirable skin compatibility or adaptability can be obtained. This is due to the pH buffer action (pH 4–5) or skin protecting property based on the natural high polymer acid structure, remarkably high water-retention characteristics, and moderate skin adhesiveness thereof.

When karaya gum is used as the above-mentioned polysaccharide, the gel composition selected is usually 20 to 70 parts by weight of karaya gum and 80 to 30 parts by weight of a polyol, such as glycerine or propylene glycol (containing 0% to 50% by weight of $H_2O$ based on the weight of the polyol), depending upon its intended use. Since the resultant gel has sufficient water-retention characteristics, an ionic agent or drug in the form of aqueous solution can be added to the gel layer before usage. The addition of electrolytes to the counter electrode is not necessarily required since gel composed of karaya gum has sufficient conductivity by itself.

When the gel layers are compounded or prepared, the same electrochemical considerations should be given as with the preparation of the so-called electrophoresis gel. Generally, the gel layer is prepared so as to provide the desired ion mobility or conductivity, depending upon the kind of the ionic agent or drug, the administered amount (dose required), the application period, the output power of the battery, the contact area to the skin, and other factors.

Examples of the preparation and composition of the conductive gel layers suitable for use in the present iontophoresis device are given below. The examples are given in reference to the conductive gel layers for the counter electrodes, however, the conductive gel layers of the working electrodes can be prepared in the same manner except that all or part of the electrolytes such as sodium chloride is replaced with the desired ionic agent or drug. The desired ionic agent or drug can be incorporated into the gel layer at the time when the gel layer is prepared or just before the iontophoresis device is actually applied to the skin.

1. A 30 g amount of powdered polyvinyl alcohol having a weight-average molecular weight of 440,000 and a saponification value of about 60% was prepared in a conventional manner. Forty grams of a 10% NaCl solution in distilled water, preheated to a temperature of 80° C., and 30 g of glycerine were added to the powdered polyvinyl alcohol. The mixture was thoroughly stirred. The resultant mixture was hot-pressed for about 20 minutes at a pressure of 0.6 kg/cm$^2$G in a hot press heated to a temperature of 80° C. Thus, a flexible sheet having a thickness of 3 mm was obtained. The flexible sheet thus obtained had a sufficient adhesiveness to the skin and a specific resistance of 0.8 kΩ·cm.

2. Electrically conductive gel layers in the form of a flexible sheet having the following compositions were prepared in the same manner as described above.

Example A

| | |
|---|---|
| Polyvinyl pyrrolidone (a weight-average molecular weight of 360,000; PVP-K90 manufactured by GAF Corporation) | 20 g |
| 10% NaCl solution in distilled water | 40 g |
| Glycerine | 40 g |

The resultant sheet had a sufficient adhesiveness to the skin and a specific resistance of 0.2 kΩ·cm.

Example B

| | |
|---|---|
| Polyvinyl formal (a weight-average molecular weight of 1,600,000, a formalization degree of 15%, and a saponification degree of the starting polyvinyl alcohol of 60%) | 15 g |
| 5% NaCl solution in distilled water | 70 g |
| Propylene glycol | 15 g |

The resultant sheet had a sufficient adhesiveness to the skin and a specific resistance of 1.0 kΩ·cm.

Example C

| | |
|---|---|
| Polyvinyl acetoacetal (a weight-average molecular weight of 440,000, an acetalization degree of 30%, and a saponification degree of the starting polyvinyl alcohol of 70%) | 40 g |
| 15% NaCl solution in distilled water | 50 g |
| Ethylene glycol | 10 g |

The resultant sheet had a sufficient adhesiveness to the skin and a specific resistance of 0.75 kΩ·cm.

3. A 20 g amount of sodium polyacrylate having a weight-average molecular weight of 3,000,000 to 5,000,000 (Aron-vis SS® manufactured by Nippon Junyaku Kabushiki Kaisha) was uniformly mixed with 12 g of a 5% NaCl solution in distilled water and 68 g of glycerine.

The resultant mixture was heated under pressure at a temperature of 80° C. for 10 minutes to provide a flexible sheet. The sheet thus prepared had a moderate adhesiveness to skin and a specific resistance of 0.5 kΩ·cm after being allowed to stand for 1 day.

4. A 30 g amount of karaya gum was uniformly mixed with 30 g of 5% NaCl solution in distilled water and 40 g of glycerine and then hot-pressed to form a sheet in the same manner as mentioned above. The specific resistance of the resultant sheet was 0.65 kΩ·cm.

5. A 20 g amount of sodium polyacrylate having a weight-average molecular weight of 3,000,000 to 5,000,000 (Aron-vis SS® manufactured by Nippon Junyaku Kabushiki Kaisha) was uniformely mixed with 80 g of a 7% NaCl solution in distilled water and then hot pressed to form a sheet in the same manner as mentioned above. The specific resistance of the resultant sheet was 0.47 kΩ·cm.

From the electrochemical point of view, when a basic agent such as propranolol, insulin, lidocaine, or cystine is used, an acidic polymer such as polyacrylic acid, methyl vinyl ethermaleic anhydride copolymer (e.g., GANTREZ® AN-169 manufactured by G.A.F. Co.), or carboxypolyethylene CARBOPOL® manufactured by Goodrich Co.) can be preferably used, as a base material for the gel layer, for obtaining a high drug introduction efficiency. Contrary to this, when an acidic agent such as ascorbic acid, salicylic acid, nitrous acid, riboflavin phosphoric acid, betamethasone phosphoric acid, or trans-retinoic acid is used, a basic polymer such as polyacrylamide can be preferably used.

An example of a gel composition suitable for use as a gel layer for propranolol is as follows:

| Composition | Parts by weight |
|---|---|
| CARBOPOL ® 491 or GANTREZ ® AN-169 | 30 |
| Glycerine | 45 |
| Water | 15 |
| Propranolol | 10 |

The composition in the form of a self-adhesive type film having a thickness of approximately 0.1 to 0.5 mm can be extremely preferably used as integral type film working and counter electrodes according to the present invention.

Furthermore, it should be noted that nonionic polymeric substances such as polyvinyl alcohol and polyvinyl pyrolidone can also provide a gel having an electrochemically relatively high efficiency.

As is clear from the above description, wide varieties of hydrophilic polymeric substances can be used, in the formation of conductive gel layers suitable for use in the present invention, by softening and plasticizing said substances with water and/or alcohols. There are no limitations on the special basic materials or the special composition thereof. Generally speaking, the gel composition is selected from those containing 10% to 70% by weight of hydrophilic polymeric substances and the remainder of water and/or polyols in order to obtain the desired shape retentiveness. Although the above-mentioned conductive gel layers have a sufficient adhesiveness to the skin by themselves, additional pressure-sensitive adhesive components such as acrylic type adhesives, and vinyl acetate emulsion type adhesives can be incorporated into the gel layers, if desired. Thus, when skin-adhesive and conductive gel layers are arranged at peripheral or edge portions of the structures, the entire structures can be firmly retained in the skin without necessitating other fixing means such as adhesive tapes.

When the conductive gel layer for the first electrode is prepared, the desired ionic agent or agents can be substituted for a portion or all of the electrolyte component (e.g., sodium chloride) in the above-mentioned gel compositions. If desired, the water-retaining member layer is freely removably structured and, when the iontophoresis device is applied to the human skin, the water-retaining portion previously impregnated with the drug solution may be placed in the predetermined portion of the structure. Furthermore, non-adhesive hydrogels such as agar gels and gelatin gels conventionally used in the field of electrophoresis can be used in lieu of the above-mentioned water-absorbable members. One example of the agar gels is as follows:

| Composition | Parts by weight |
| --- | --- |
| Agar powder | 4.0 |
| Purified water | 100.0 |
| Vitamin C | 5.0 |
| (Ascorbic acid: its Na salt = 1:1) | |

Figure 1:
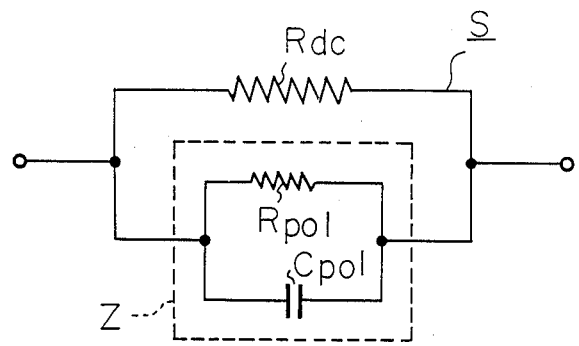
FIG. 1 is a circuit diagram equivalent to the human skin.
Figure 2A:
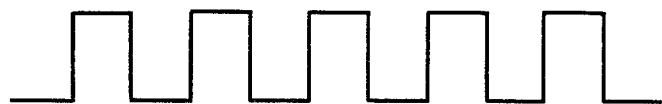
Figure 2B:
Figure 2C:

These non-adhesive hydrogels such as agar gels can be previously laminated in the device structure or, as mentioned above, placed when the device is used. It should be noted that, when nonadhesive hydrogels such as agar gels are used, skin adhesive means such as pressure-sensitive adhesive tapes should be arranged on, for example, the outer circumferential portion of the present iontophoresis device, as shown in FIG. 1.

Ionic Agent or Drug

Various kinds of agents or drugs can be used in the present iontophoresis device so long as they can dissociate into ions. Examples of ionic agents or drugs usable in the present invention are potassium iodide, procaine hydrochloride, methacholine, various skin vitamins such as vitamins $B_1$, $B_2$, $B_6$, and C, histamine, sodium salicylate, dexamethasone, betamethasone phosphate, epinephrine, hydrocortisone, idoxuridine, propanolol, pranolol, nitrites, bleomycin, undecylenic acid salts, sodium dexamethasone phosphate, sodium prednisolone phosphate, alimemazine, chlorpheninamine maleate, clemastine, glibenclamide, colchicine, diclofenac sodium, chlorpromazine, chlordiazepoxide, clonazepam, desipramine, imipramine, atropine sulfonate, ergotamine, nifedipine, alprenolol, indenolol, oxphenolol, isoprenaline, betanidine, chlonidine, guanethidine, hydralazine, prazosin, ephedrine, salbutanol, terbutaline, and metoclopramide.

The present invention will now be further illustrated by, but is by no means limited to, the following application examples.

Application Example 1

Conductive gel layers for working and counter electrodes having a thickness of 1.5 mm and an area of 48 cm² were prepared from a viscoelastic gel composition comprising 20% by weight of the above-mentioned CARBOPOL ® 491, 30% by weight of distilled water, and 40% by weight of glycerine. The gel layer of the working electrode further contained 5% by weight of sodium salicylate. The gel layer of the counter electrode, further contained 3% by weight of sodium chloride.

These gel layers were integrally assembled by laminating a power supply unit generating a therapeutic pulse having a frequency of 10 kHz (duty ratio of 30%) connected to a 6V electric source. An aluminum foil was used as a current-distribution conductive member layers.

The iontophoresis device of this example can be used as an analgesic and antiphlogistic agent. However, since the so-called galvanization effecting vasodilative function is also conducted by simultaneous application of a bias voltage within the non-skin irritation range or by maintaining a certain amount of the residual polarization voltage within the non-skin irritation range, it should be noted that this iontophoresis device exhibits remarkable synergestic effects on disorders such as neutralgia, arthralgia, and rheumatoid arthralgia.

Application Example 2

1. Metoprolol tartrate (Antiarrhythmic drug)

Electrode sheets having a thickness of each electrode of 1 mm and an area of each electrode of 50 cm² and containing 10% of metoprolol tartrate (Ciba-Geigy Co.) in the composition shown in Table 1 were applied to healthy men (I: Age 31, Body weight 75 kg; II: Age 39, Body weight 56 kg).

TABLE 1

| Composition | % by weight |
| --- | --- |
| ACCOFLOC A-100*1 | 15 |
| ACCOFLOC C-480*2 | 5 |
| Glycerine | 60 |
| Distilled water | 20 |

*1Copoly(acrylamide-acrylic acid) manufactured by Mitsui Cyanamide Co.
*2Polyacrylamide manufactured by Mitsui Cyanamide Co.

The working and counter electrodes were adhered to the left forearms of the test persons with a distance of about 1 cm between the working electrode and the counter electrode. Thus, iontophoresis was carried out according to the present depolarization method under the conditions of a frequency of 50 kHz, a duty ratio of 20% (pulse width=4 μs), and a voltage of 10V. The average pulse current was 50 mA.

Sample of blood in an amount of 20 ml were taken from the right-arm vein by a heparin treated tube at 0 hr, 4 hrs, and 8 hrs from the initiation of the test. The concentrations of metoprolol tartrate in the blood plasma fraction were determined by a gas-liquid chromatography method according to Degen & Riess (J. Chromat. 121, 72–75 (1976)). The analysis was carried out by using a Hitachi model 163 analyzer provided with an ionization detection device (manufactured by Hitachi, Ltd.) under the conditions of an injection temperature of 220° C. and an oven temperature of 200° C. A QF-1 glass column having a length of 2 m and packed with 2% silicon was used.

The results are shown in Table 2. No skin irritation such as rubefaction in the skin occurred during the test periods.

TABLE 2

| Test Person | Time (hrs) | | |
| --- | --- | --- | --- |
| | 0 | 4 | 8 |
| I | 0 | 80* | 121* |

TABLE 2-continued

| Test Person | Time (hrs) | | |
| --- | --- | --- | --- |
| | 0 | 4 | 8 |
| II | 0 | 87* | 87* |

*ng/ml

2. Diclofenac sodium (Anti-inflammatory agent)

Electrode sheets each having a thickness of 1 mm and an area of 50 cm² and containing 2% of diclofenac sodium (Ciba-Geigy Co.) in the composition shown in Table 3 were applied to a healthy man to be tested having an age of 35 and a body weight of 55 kg.

TABLE 3

| Composition | % by weight |
| --- | --- |
| ACCOFLOC N-100(P)*1 | 15 |
| Kuraya gum | 15 |
| 1,2-propylene glycol | 20 |
| Glycerine | 20 |
| Distilled water | 30 |
| | 100 |

*1Polyacrylamide manufactured by Mitsui Cyanamide Co.

The electrode sheets were adhered to the left forearm of the test person with a distance of about 1 cm between the two electrode sheets. Thus, the iontophoresis was carried out under the same operation conditions as mentioned above. After 5 hours, a 20 ml blood sample was obtained.

The concentration of dicrofenac sodium in the blood plasma fraction was determined by a gas-liquid chromatography method according to Geiger, Degan, and Sioufi (J. Chromat. 111, 293–298 (1976)), which was modified to a small extent. The analysis was carried out by using a Hitachi model 163 analyzer provided with an ionization detection device (manufactured by Hitachi, Ltd.) under the same temperature conditions. A QF-1 column having a length of 2 m and packed with 2% silicon was used.

As a result, the dicrofenac sodium level in the blood plasma after 5 hours was about 128 ng/ml.

It is clear that the plaster type iontophoresis device illustrated in Application Example 1 is effective for curing various skin disorders and for injecting various cosmetic skin nutrients. For example, self-adhesive conductive gel layers for both electrodes having a thickness of 1.5 mm and an area of about 1.2 cm² are prepared from a viscoelastic gel comprising 20% by weight of GANTREE® AN-169, 15% by weight of a 20% NaCl solution in distilled water, and 65% by weight of glycerine. Before the application, 1 to several mililiters of a 3% aqueous solution of sodium ascorbate (stored in an ampule) was dropwise impregnated into the conductive gel layer and, then, the entire iontophoresis device structure is adhered to the affected skin to effect the iontophoresis treatment.

As is well-known in the art, vitamin C (ascorbic acid) or the derivatives thereof such as sodium ascorbate are effective for curing chromatodermatosis such as the so-called moth patch, freckle, and various melanosises. However, as mentioned above, conventional iontophoresis has not become popular due to the troublesome application although it is known that iontophoresis is a very effective method for curing chromatodermatosis and the like. Contrary to this, the present iontophoresis device can be very effectively and advantageously used for curing various skin disorders and for injecting various cosmetic skin nutrients by a very simple operation. This constitutes a dramatic progress in this field.

In addition to the above-exemplified hydrophilic polymeric substances usable as a gel layer material, various known hydrophilic polymeric substances usable as so-called bioelectrode materials can be also used. Such materials are disclosed in, for example, Japanese Unexamined Patent Publication (Kokai) Nos. 52-95895, 54-77489, 55-52742, 55-81635, 55-129035, 56-15728, 56-36939, 56-36940, 56-60534, 56-89270, 56-143141, 57-28505, 57-49431, 57-52463, 57-55132, 57-131428, 57-160439, 57-164064, 57-166142, 57-168675, 57-4569, and 58-10066, and Japanese Unexamined Utility Model Publication (Kokai Nos. 54-80689, 56-135706, 56-138603, 57-93305, 57-179413, and 57-185309. These hydrophilic polymeric substances can be used as a basic substance of the gel layer in the present iontophoresis device by appropriately adjusting the water content thereof. Typical examples of such materials are polyethylene glycol, carboxy polymethylene, methyl cellulose, sodium alginate, and polyethylene oxides.

Thus, any hydrophilic polymeric substances which can be softened and plasticized with water and/or polyols to form viscoelastic gels, desirably having an adhesiveness to the skin, can be used as the basic gel material of the conductive gel layers of the present iontophoresis device. These substances are generally selected taking into consideration the compatibility thereof with the ionic agent or drug to be used, the compatibility with the skin, and the electrical conductivity. These gel layers can be discarded or reused.

The invention has been described in detail with particular reference to certain preferred embodiments thereof, but it will be understood that variations and modifications can be effected within the spirit and scope of the invention.

I claim:

1. In an iontophoresis device including an electric power source, a working electrode and a counter electrode, the improvement which comprises: said device having a pulse generator means which is driven by said electric power source for producing a therapeutic pulse voltage of high frequency between said working and counter electrode and a shortcircuiting means for shortcircuiting said working and counter electrodes in an intermission period of said therapeutic pulse voltage for a selected duration to depolarize polarized potentials therebetween to a predetermined low level close to a base line, thereby producing iontophoresis by high frequency pulse current without skin irritations.

2. The device of claim 1 which further includes means for controlling output current.

3. The device of claim 1 which further includes a means for recovering residual charges stored in the skin as a result of the polarization capacity thereof.

4. The device of claim 3, wherein said means for recovering the residual charges is an inductor for discharging and simultaneously recovering the residual charges of the skin by L-C resonance between the inductance of said inductor and the capacitance of the skin.

5. The device of claim 1, wherein said therapeutic pulse voltage has a frequency in the range of 1 kHz to 500 kHz.

6. The device of claim 5, wherein said therapeutic pulse voltage has a duty ratio in the range of 0.1 to 0.7.

7. The device of claim 6, wherein said shortcircuiting means is designed to depolarize the polarized potentials between said working and counter electrodes to a level less than 3V.

8. The device of claim 1 which further includes a voltage converter for amplifying voltage from said electric source.

* * * * *